(12) United States Patent
Hoffman et al.

(10) Patent No.: US 7,252,730 B2
(45) Date of Patent: Aug. 7, 2007

(54) METHOD AND APPARATUS FOR APPLYING AN ELASTIC MEMBER

(75) Inventors: John W. Hoffman, Appleton, WI (US); Patrick J. Nahm, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 216 days.

(21) Appl. No.: 10/750,016

(22) Filed: Dec. 30, 2003

(65) Prior Publication Data

US 2005/0145322 A1 Jul. 7, 2005

(51) Int. Cl.
*A61F 13/15* (2006.01)

(52) U.S. Cl. ............... 156/164; 156/160; 156/229; 156/496

(58) Field of Classification Search ........ 156/160–167, 156/264, 229, 495, 496; 604/386, 396, 358, 604/387, 389, 394, 385.3; 428/373; 442/328, 442/329
See application file for complete search history.

(56) References Cited

U.S. PATENT DOCUMENTS

| | | | |
|---|---|---|---|
| 3,833,973 A | | 9/1974 | Schwarz |
| 4,642,151 A | * | 2/1987 | Coenen ............... 156/164 |
| 4,704,116 A | | 11/1987 | Enloe |
| 4,770,656 A | | 9/1988 | Proxmire et al. |
| 4,808,176 A | | 2/1989 | Kielpikowski |
| 4,822,435 A | | 4/1989 | Igaue et al. |
| 4,834,738 A | | 5/1989 | Kielpikowski et al. |
| 4,834,740 A | | 5/1989 | Suzuki et al. |
| 4,842,596 A | | 6/1989 | Kielpikowski et al. |
| 4,846,825 A | | 7/1989 | Enloe et al. |
| 4,916,005 A | | 4/1990 | Lippert et al. |
| 4,925,520 A | * | 5/1990 | Beaudoin et al. ........... 156/494 |
| 4,936,840 A | | 6/1990 | Proxmire |
| 4,940,464 A | * | 7/1990 | Van Gompel et al. ...... 604/396 |
| 4,943,340 A | * | 7/1990 | Ujimoto et al. ............ 156/496 |
| 4,964,860 A | * | 10/1990 | Gipson et al. ............ 604/391 |
| 5,000,806 A | | 3/1991 | Merkatoris et al. |
| 5,061,261 A | | 10/1991 | Suzuki et al. |
| 5,064,489 A | | 11/1991 | Ujimoto et al. |
| 5,176,672 A | | 1/1993 | Bruemmer et al. |
| 5,296,080 A | | 3/1994 | Merkatoris et al. |
| 5,308,345 A | | 5/1994 | Herrin |
| 5,462,541 A | | 10/1995 | Bruemmer et al. |
| 5,496,298 A | | 3/1996 | Kuepper et al. |
| 5,527,302 A | | 6/1996 | Endres et al. |
| 5,545,158 A | * | 8/1996 | Jessup ................. 604/385.3 |
| 5,560,793 A | | 10/1996 | Ruscher et al. |

(Continued)

FOREIGN PATENT DOCUMENTS

EP 0 634 766 A1 1/1995

(Continued)

*Primary Examiner*—Jeff H. Aftergut
(74) *Attorney, Agent, or Firm*—Randall W. Fieldhack (57) ABSTRACT

A method and apparatus for stretching an elastic member and applying it to an article web include a pair of wheels that rotate the elastic member. In particular, the pair of wheels engages the elastic member at an entry location on the pair of wheels and rotates the elastic member from the entry location to an exit location on the pair of wheels. In addition, an absorbent article may include at least one elastic member provided by the method and apparatus.

13 Claims, 3 Drawing Sheets

U.S. PATENT DOCUMENTS

| | | |
|---|---|---|
| 5,569,232 A | 10/1996 | Roe et al. |
| 5,705,013 A | 1/1998 | Nease et al. |
| 5,711,832 A * | 1/1998 | Glaug et al. ............... 156/73.1 |
| 5,853,881 A | 12/1998 | Estey et al. |
| 5,897,545 A | 4/1999 | Kline et al. |
| 5,910,136 A | 6/1999 | Hetzler et al. |
| 5,957,908 A | 9/1999 | Kline et al. |
| 6,022,430 A * | 2/2000 | Blenke et al. ............. 156/73.1 |
| 6,022,431 A * | 2/2000 | Blenke et al. ............. 156/73.1 |
| 6,111,168 A | 8/2000 | Raboy |
| 6,120,487 A | 9/2000 | Ashton |
| 6,278,037 B1 | 8/2001 | Schmidt et al. |
| 6,284,081 B1 * | 9/2001 | Vogt et al. .................. 156/163 |
| 6,287,287 B1 * | 9/2001 | Elsberg ................ 604/385.03 |
| 6,336,922 B1 * | 1/2002 | VanGompel et al. ..... 604/385.3 |
| 6,359,192 B1 | 3/2002 | Schmidt et al. |
| 6,406,466 B1 | 6/2002 | Pozniak et al. |
| 2001/0042591 A1 * | 11/2001 | Milner et al. ............... 156/252 |
| 2002/0019616 A1 * | 2/2002 | Thomas ...................... 604/373 |

FOREIGN PATENT DOCUMENTS

| | | |
|---|---|---|
| EP | 0 773 769 B1 | 11/2000 |
| EP | 0 869 756 B1 | 10/2002 |
| GB | 2 291 783 | 7/1996 |
| JP | 01-132803 A | 5/1989 |
| JP | H3-114223 | 11/1991 |
| JP | 04-067864 A | 3/1992 |
| JP | H4-32718 | 3/1992 |
| JP | 05-137754 A | 6/1993 |
| WO | WO 00/19950 A1 | 4/2000 |
| WO | WO 00/19951 A1 | 4/2000 |
| WO | WO 00/20206 A1 | 4/2000 |
| WO | WO 00/20207 A1 | 4/2000 |
| WO | WO 00/37006 A1 | 6/2000 |
| WO | WO 01/39709 A1 | 6/2001 |
| WO | WO 0213741 A1 * | 2/2002 |

* cited by examiner

METHOD AND APPARATUS FOR APPLYING AN ELASTIC MEMBER

FIELD OF THE INVENTION

The present invention relates to a method and apparatus for applying an elastic member to a moving web, such as a web of interconnected absorbent articles, as well as articles including the elastic member. In particular, the present invention is directed to a method and apparatus for applying a zone stretched elastic member to an absorbent article, as well as articles including a zone stretched elastic member.

BACKGROUND OF THE INVENTION

Articles, particularly disposable absorbent articles may advantageously include portions that are elastic. These portions of elastic material may improve the fit, comfort and containment characteristics of the absorbent articles in use. In certain situations, these portions may be provided by separately attached elastic members that are applied to the chassis of the absorbent article at some point in the manufacturing process. For example, portions of an absorbent article such as a disposable diaper that may be provided by a separately attached elastic member are the waist elastics and ear portions of the article.

Several methods and apparatus exist to apply separately attached components on an absorbent article, such as applicator rolls, cut and place modules, and the like. Nonetheless, these existing methods and apparatus may, in certain circumstances, not be entirely satisfactory. For instance, many of the processes and apparatuses do not elongate an elastic component prior to application. In the instances where an elastic component is elongated by a process and apparatus prior to application, the entire component is generally elongated, rather than being elongated in only particular areas, (i.e., zone stretched). Moreover, when it is desired to apply a number of components to an article in a converting process, it is often necessary to include that number of separate application processes and apparatus.

Therefore, in one example, in order to apply a waist elastic to an absorbent article that gathers the waist edge, and then apply a pair of elastic ears, the application of each component may generally require a discrete apparatus and a discrete number of steps. Thus, as components are added to the article, and as a result, further process steps are also added to the manufacturing process, the cost and complexity of the process and converting line can likewise be increased.

Accordingly, despite attempts to provide a method and apparatus for applying components to an article web in a converting process, such as those described above, these attempts have not been entirely satisfactory. That is, there remains a need for a method and apparatus capable of zone stretching an elastic member. Further, there remains a need in certain instances to provide a method and apparatus that is capable of applying a zone stretched elastic member to an article web. Still further, there remains a need for articles that include zone stretched components.

SUMMARY OF THE INVENTION

In response to the problems and difficulties discussed above, a new distinctive method, apparatus, and article have been discovered. In one aspect the present invention concerns a method for applying an elastic member to an article web defining a pair of article web side edges. The method includes:

i) providing an elastic member, wherein at least a portion of the elastic member is elongatable in at least a cross machine direction and defines an elastic member width;
ii) moving the elastic member in a machine direction along an elastic member web path;
iii) providing a pair of rotatable wheels in the elastic member web path, the pair of wheels defining:
   a) a pair of inboard edges,
   b) a pair of outboard edges opposite the inboard edges,
   c) an elastic member entry location having an elastic member entry location width that is less than the elastic member width, and
   d) an elastic member exit location having an elastic member exit location width that is greater than the elastic member entry width;
iv) engaging the elastic member with the pair of wheels at the elastic member entry location wherein a portion of the elastic member is located beyond each of the inboard edges of the pair of wheels thereby defining a pair of outboard portions of the elastic member and an inboard portion of the elastic member;
v) rotating the elastic member with the pair of wheels; and
vi) applying the elastic member to the article web proximate the elastic member exit location wherein the outboard portions of the elastic member extend beyond the article web side edges.

In another aspect, the present invention concerns an apparatus for applying an elastic member to an absorbent article. The apparatus includes:

i) a pair of rotatable wheels; the pair of wheels define:
   a) a pair of inboard edges,
   b) a pair of outboard edges,
   c) an outer surface,
   d) an elastic member entry location having a first distance between the inboard edges, and
   e) an elastic member exit location having a second distance between the inboard edges that is larger than the first distance;
ii) a wheel drive system connected to the pair of wheels for rotating the wheels about the central axis; and
iii) a vacuum system connected to each of the wheels wherein the vacuum system includes a plurality of openings in at least a portion of the outer surface and at least one source of vacuum.

In yet another aspect, the present invention concerns a method for attaching an elastic member to an article. The method includes: providing an article web having opposing article web side edges and defining between the article web side edges a chassis width; providing a plurality of elastic members each having an inboard portion and a pair of outboard portions; and stretching the inboard portion such that the elastic members define a stretched length that is greater than the chassis width. The method also includes attaching the inboard portion to the article web between the article web side edges.

In still yet another aspect, the present invention concerns a disposable absorbent article which defines a longitudinal direction, a lateral direction, an exterior surface, an interior surface opposite the exterior surface, a pair of laterally opposed side portions and a pair of longitudinally opposed front and rear portions. The absorbent article includes an elastic member having an inboard portion and a pair of outboard portions. The inboard portion is elongated and applied to one of the portions thus contracting the one of the portions, and the outboard portions of the elastic member extend beyond the side portions of the absorbent article to provide a pair of ears. The absorbent article also includes a pair of fasteners adapted to releasably connect the front and rear portions.

Accordingly, the present invention provides a method and apparatus may apply an elastic component on a web that has been elongated in particular areas. As such, the single component may be configured to replace multiple components thereby potentially reducing manufacturing complexity and material costs. Moreover, the apparatus of the present invention can replace multiple devices in a production process, thus reducing asset costs and potentially reducing the overall footprint of a production line. Still further the present invention provides an absorbent article including an elastic member that has been zone stretched.

It is understood that both the foregoing general description and the following detailed description are exemplary and are intended to provide further explanation of the invention claimed. The accompanying drawings, which are incorporated in and constitute part of this specification, are included to illustrate and provide a further understanding of the process and apparatus of the present invention. Together with the description, the drawings serve to explain the various aspects of the invention.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

The present invention is directed to a method and apparatus for applying an elastic member to a moving web in a simple and economical process. In particular, the present invention is directed to a method and apparatus for applying an elastic member to a moving web where a portion of the elastic member is stretched when applied while other portions of the elastic member remain in a substantially relaxed or unstretched state when applied. Still more particularly, the present invention is directed to a method and apparatus for applying an elastic member to a moving web where the discrete member may perform the same function as is provided by separate, multiple components on an absorbent article.

For example, the method and apparatus of the present invention may be used to apply a pair of stretchable outer ears and a gathered stretchable waist band to an absorbent article using a single process and apparatus and a discrete piece of material. As such, the present invention is directed to solving the problem of providing a method and apparatus that is capable of zone stretching a component, particularly an elastic component. Moreover, the present invention is directed to solving the problem of providing a single method and apparatus that is capable of producing an elastic member having multiple portions that have distinct elongations. In particular aspects, the present invention may be directed to providing a single method and apparatus that is capable of applying a component having multiple functions on an article web. In yet other aspects, the present invention may also be directed to replacing multiple processes and apparatuses with a single process and apparatus. In still yet other aspects, the present invention is directed to an absorbent article including a zone stretched elastic member.

As such, the present invention is directed to a method for applying an elastic member to an article web, and specifically is suited for applying a zone stretched elastic member to the article web. The method and apparatus may be particularly suited for use in applying components to an absorbent article, such as waist elastics or elastic ears. In addition, the method and apparatus may be configured to apply a zone stretched elastic member to an article web where the elastic member is capable of performing multiple functions.

Accordingly, the principles of the present invention can be used with a variety of material webs that can be incorporated into an even greater variety of products. For ease of explanation, the description hereafter will be in terms of an elastic member for use in a disposable absorbent article, specifically, a disposable diaper. Typically, disposable articles are intended for limited use and are not intended to be laundered or otherwise cleaned for reuse. For example, disposable absorbent articles that the present invention is equally adaptable for use with include training pants, feminine care products, incontinence garments, changing pads, surgical drapes, adult incontinent products, feminine care products, personal hygiene products, other personal care or health care garments, and the like.

As used herein, the term "cross-machine direction" means that direction or axis of the product or material generally perpendicular to the machine direction, and generally corresponds to the lateral direction, and is indicated in the drawings by reference number 29.

As used herein, the terms "elastomeric" or "elastic" mean that property of a material or composite by virtue of which it tends to recover its original size and shape after removal of a force causing a deformation or elongation.

As used herein, the term "machine direction" means that direction or axis of the product or material in which the product or material is produced or the axis corresponding to the direction of the machine operations. The machine direction generally corresponds to the longitudinal direction and is indicated in the drawings by reference numeral 28.

Figure 1:
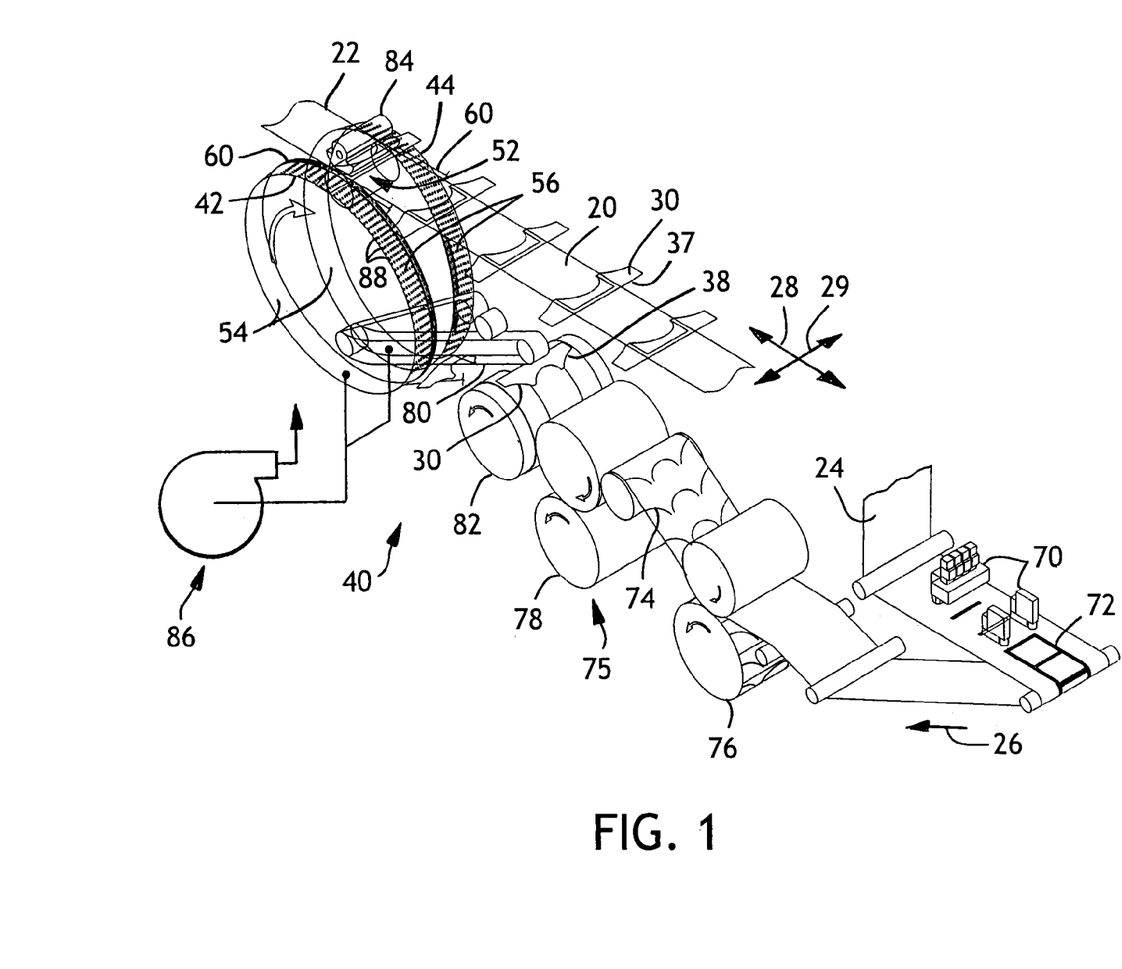
FIG. 1 representatively illustrates a perspective schematic view of a method and apparatus of the present invention.

Referring now to FIG. 1, there is representatively illustrated an aspect of the method and apparatus 40 of the present invention. As will be described in greater detail below, the apparatus 40 includes a pair of rotatable wheels 42 and 44. Each of the wheels 42 and 44 defines an axis 43 and 45. Further, in aspects where the wheels do not include a substantially solid construction, the wheels 42 and 44 define an inner circumferential surface 54 and an outer circumferential surface 56. The pair of wheels 42 and 44 also defines a pair of inboard edges 46 and a pair of outboard edges 48. Further, the pair of wheels 42 and 44 defines an elastic member entry location 50 having an elastic member entry width and an elastic member exit location 52 having an elastic member exit width that is greater than the elastic member entry width. An elastic member 30 is provided to and is engaged by the pair of wheels 42 and 44 at the elastic member entry location 50. The pair of wheels 42 and 44 is configured to rotate about their axes 43 and 45, and as such, the elastic member 30 is rotated by the pair of wheels and applied to an article web 20 at the elastic member exit location 52.

As will be discussed in greater detail below, the article web 20 may be a continuously moving web of interconnected absorbent articles. Alternatively, the article web 20 may be any substantially continuous portion of material that may benefit from the addition of separately attached components, such as a woven or nonwoven material, and may include several layers of material or one layer of material, or combinations thereof. The article web 20 may have a pair of opposed article web side edges 22 and define between the article web side edges 22 a chassis width.

Figure 2:
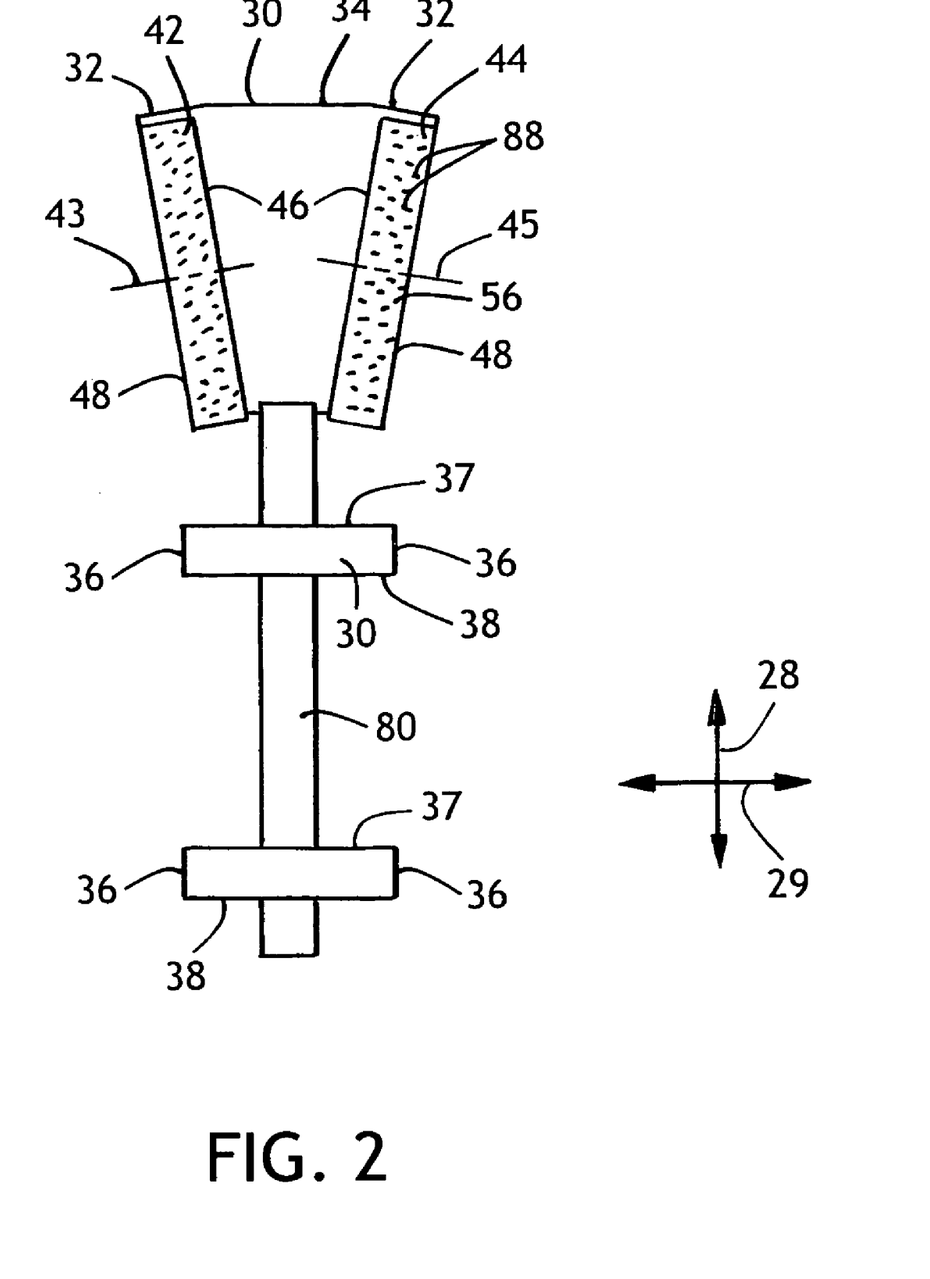
FIG. 2 representatively illustrates a top plan view of an aspect of the method and apparatus of the present invention.

As representatively illustrated in FIGS. 1 and 2, the pair of rotatable wheels 42 and 44 are provided by a first wheel 42 and a second wheel 44. The wheels 42 and 44 are spaced from each other to provide an entry location width and an exit location width. In particular, the wheels 42 and 44 are spaced such that the exit location width is greater than the entry location width. Moreover, the entry location width may advantageously be less than the elastic member width. Thus, as will be discussed in greater detail below, at least a portion of the elastic member 30 may be elongated upon the wheels 42 and 44 of the method and apparatus 40 of the present invention as it travels from the entry location 50 to the exit location 52.

The wheels may be suitably provided by various materials as is well known in the art. For example, the wheels may be made of various plastics, aluminum, stainless steel, carbon fiber materials, and the like or combinations thereof.

The pair of wheels 42 and 44 may simultaneously rotate about their axes 43 and 45 at substantially the same speed in order to rotate the elastic member 30 from the entry location 50 to the exit location 52. The wheels 42 and 44 may be driven independently or may both be connected to a common drive system (not shown). For example, each of the wheels 42 and 44 may be independently driven by a motor. Alternatively, if driven by a common drive system, the wheels 42 and 44 may each be connected to a single drive shaft or motor using belts, sheaves, gears, chains, direct coupling or combinations thereof. Generally, the wheels 42 and 44 may advantageously employ a common drive system for simplicity and to ensure that they rotate at the same speed.

As can be readily appreciated, the wheels 42 and 44 may be of various sizes. That is, it may be desirable for the wheels 42 and 44 to be at least a certain diameter such that, in use, when the wheels rotate, the elastic member 30 being rotated may be elongated at a more moderate pace as compared to if the elastic member 30 were being rotated on a pair of wheels of a smaller diameter. Alternatively, space in a production facility is commonly at a premium, and as such, machine components may be designed to occupy as little space as possible while remaining effective. Balancing these concerns, the diameter of the wheels 42 and 44 may be between 0.3 meters and 2.0 meters.

As representatively illustrated in FIG. 1, the wheels 42 and 44 may substantially be the same diameter. Alternatively, in certain aspects, the wheels 42 and 44 may be of differing diameters. Generally, the wheels may advantageously each be the same diameter for improved performance. Similarly, in the illustrated embodiments, the wheels 42 and 44 are both substantially arcuate in shape. As such, the wheels 42 and 44 may be circular, oval, or elliptical in shape. In particular aspects, the wheels 42 and 44 are each generally circular.

As mentioned above, in the illustrated aspects, the wheels 42 and 44 may each further define an inner surface 54 and an outer surface 56 opposite the inner surface. As may be appreciated, however, the wheels 42 and 44 may alternatively be substantially solid, and as such may not include an inner surface. The outer surface 56 is that portion of the wheels 42 and 44 that is configured to engage the elastic members 30 for application to the article web 20 in use.

In a particular aspect, at least a portion of the outer surface 56 of each wheel 42 and 44 may be textured to define a surface roughness which can assist in gripping and maintaining the position of the elastic member 30 on the outer surface 56 of the wheels 42 and 44, particularly when at least a portion of the elastic member 30 is being stretched. As used herein, the term "surface roughness" is the surface roughness of a material as determined by conventional methods known to those skilled in the art. One such method utilizes a profilometer to detect the surface roughness. The stylus of the profilometer is drawn across the textured surface a distance of 1.27 centimeters. The profilometer measures the number of peaks and valleys on the surface as well as the magnitude of each. The profilometer automatically calculates the surface roughness as a Roughness Average ($R_a$) which is the arithmetic average of the measured profile height deviations taken within the sampling length and measured from the graphical centerline.

At least a portion of the outer surface 56 of each wheel 42 and 44 may define a surface roughness of at least about 3 micrometers, desirably at least about 10 micrometers and more desirably at least about 15 micrometers. For example, the outer surface 56 may have a surface roughness of from 5 to 50 micrometers and desirably from 15 to 25 micrometers. To achieve the surface roughness, the outer surface 56 of each wheel 42 and 44 may also include a coating such as a plasma coating as are known to those skilled in the art.

To further assist in maintaining the elastic members 30 on the outer surface 56 of the wheels 42 and 44, the method and apparatus 40 of the present invention may include a vacuum system 86 connected to each of the wheels 42 and 44. This system may include the outer surface 56 may also include a plurality of openings 88 in at least a portion of the outer surface 56 of the wheels 42 and 44 (and desirably from the elastic member entry location 50 to the elastic member exit location 52) through which a relatively low pressure or vacuum can be drawn. As such, engaging the elastic member 30 may include holding the elastic member 30 on the outer surface 56 of the pair of wheels 42 and 44 with low pressure or vacuum. The number and pattern of the openings 88 through which the vacuum may be drawn may vary depending upon the size of the wheels 42 and 44, the shape and size of the elastic member 30 and the desired location of the elastic member 30 on the wheels 42 and 44. If vacuum is desired, typically only a relatively small amount of vacuum is needed to assist in maintaining the elastic member 30 in position upon the outer surface 56 of the wheels 42 and 44. For example, typically no more than 20 inches of water and desirably only from 0 to 10 inches of water are required to assist in maintaining the elastic member 30 in position upon the outer surface 56. This is particularly the case where the outer surface 56 may be textured as described above, or in configurations where transfer bands 60 are utilized, as will be described in greater detail below.

If vacuum is desired, the vacuum may be drawn through the openings 88 in the outer surface 56 by a vacuum system 86 that may include at least one source of vacuum. For example, conventional techniques for drawing a vacuum as are known to those skilled in the art may be used, such as a fan system, a compressed air venturi system, a pressure blower, and the like or combinations thereof. The vacuum system 86 may be connected to each wheel 42 and 44 may also be controlled such that a vacuum is only being drawn from the outer surface 56 of each wheel 42 and 44 where the elastic member 30 travels from entry location 50 to exit location 52. For example, the vacuum may be activated on the wheels 42 and 44 just prior to where the elastic member 30 engages the wheels 42 and 44 at the entry location 50 and inactivated immediately after the exit location 52 where the elastic member 30 is applied to the article web 20.

The method and apparatus 40 of the present invention may further include a pair of transfer bands 60. In configurations where transfer bands 60 are included, each one of the transfer bands 60 is associated with one of the wheels 42 and 44 and may individually wrap at least a portion of one of the pair of wheels 42 and 44. The transfer bands 60 may advantageously assist with the engagement of the elastic member 30 onto the wheels 42 or 44. Thus, engaging the elastic member 30 with the pair of wheels 42 and 44 may include holding the elastic member 30 on the outer surface 56 of the wheels 42 and 44 with the pair of transfer bands 60. Therefore, the bands may generally wrap the wheels 42 and 44 at least from the entry location 50 to the exit location 52. Accordingly, when the elastic member 30 engages the wheels 42 and 44 the bands may also begin wrapping the wheels 42 and 44 thereby providing more secure engagement between the elastic member 30 and wheels 42 and 44 by holding the elastic members 30 against the outer surfaces 56 of the wheels 42 and 44. Conversely, at the exit location 52, the transfer bands 60 no longer contact the wheels 42 and 44 thus facilitating the application of the elastic members 30 to the web 20.

As has been discussed above, the method and apparatus 40 of the present invention may be utilized to apply an elastic member 30 to a continuously moving article web 20. As representatively illustrated in FIGS. 2 and 3, the elastic members 30 of the present invention define a pair of side edges 36, a leading edge 37, and a trailing edge 38. Further, the elastic members 30 may be of various shapes and sizes, as are well known in the art. For example, as representatively illustrated in FIG. 2, the elastic members 30 may be generally rectangular. Alternatively, the elastic members 30 may be triangular, elliptical, or other various shapes as are well known in the art, or combinations thereof.

In one aspect, the elastic member may include one or more edges 36, 37, and 38 that are curvilinear. For instance, as representatively illustrated in FIGS. 1 and 3, the elastic member may be configured to have side edges 36 that are generally rectilinear with reference to the leading edge 37, and that are generally smaller than the leading edge 37 to provide at least in part a rectangular shape, while the trailing edge 38 may be curvilinear. In particular, the trailing edge 38 may be arcuate, defining a concave shape or a convex shape.

Figure 3:
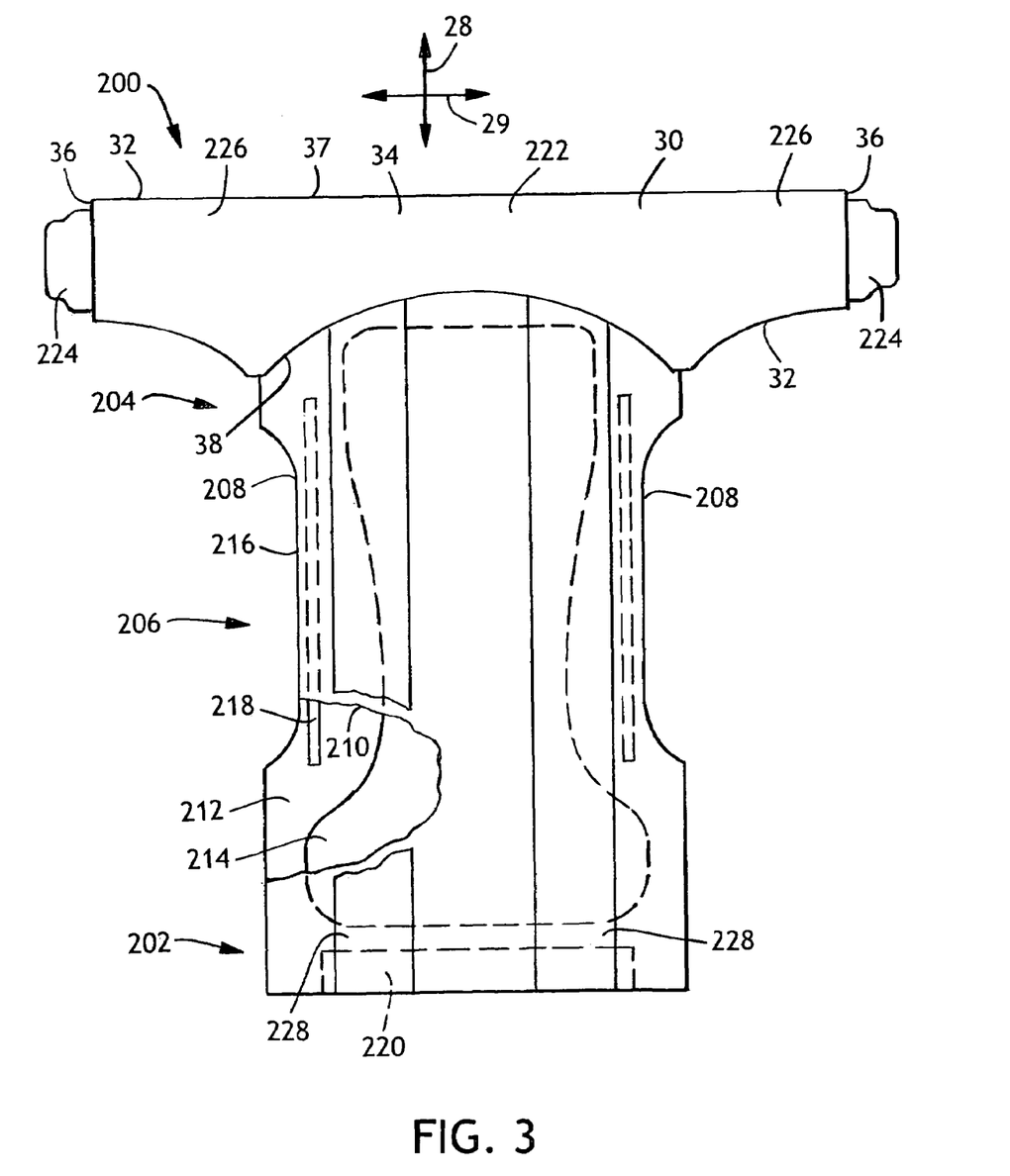
FIG. 3 representatively illustrates a diaper that includes an elastic member applied by the method and apparatus of the present invention.

Alternatively the trailing edge 38 may include multiple curves, as representatively illustrated in FIGS. 1 and 3, thus defining a "w" shape. When the trailing edge is configured in such a manner, it can assist the elastic member 30 in effectively performing the same function as several different components that may be included on an absorbent article. In such a configuration, manufacturing efficiency is improved due to the reduction of components that need to be added to an absorbent article, and raw material costs are also likewise reduced. In yet other alternatives, the leading edge 37 or side edges 36 may be curvilinear. In particular, the "w" shape may provide an elastic member 30 that provides a tailored fit to the wearer when the article 20 is placed upon a wearer in use.

In the various aspects of the present invention, the elastic members 30 may also define an inboard portion 34 and a pair of outboard portions 32 located on either side of the inboard portion 34, adjacent the side edges 36. The various portions 32 and 34 of the elastic member 30 of the present invention are generally defined by the interaction of the elastic member 30 with the wheels 42 and 44 of the present invention 40. In particular and as will be discussed below, the areas of the elastic members that are engaged by the wheels and are thus located outward from each of the inboard edges 46 of the wheels 42 and 44 generally correspond to the outboard portions 32. Conversely, the area of the elastic member 30 located between and not contacting the wheels 42 and 44, and are thus inward from the inboard edges of the wheels 42 and 44, generally corresponds to the inboard portion 34 of the elastic member. As used herein, "inward" and "outward" refer to positions relative to the centerline parallel to longitudinal or machine direction 28 of the elastic member 30, and in particular closer to or away (respectively) from the centerline of the elastic member 30.

As mentioned above, the elastic members 30 may define various shapes for improved performance. These arrangements may be configured to compliment the different portions 32 and 34 of the elastic member 30. By way of example, when the trailing edge of the elastic member 30 defines a "w" shape, the areas of the elastic member 30 that are above the outer arms of the "w" may be the outboard portions 32 as representatively illustrated in FIG. 3.

The elastic members 30 that are applied by the method and apparatus 40 of the present invention may be made of any suitable material having elastic properties. Moreover, the elastic members 30 of the different aspects of the present invention may be provided by a single material or a combination of materials. Likewise, the elastic members 30 may be provided by a single layer or multiple layers of material that are laminated together. Examples of suitable materials for making the elastic members 30 include films or layers of natural rubber, synthetic rubber, or thermoplastic elastomeric polymers, and can be panels, or single, or multiple threads or filaments or ribbons thereof. These materials may also be heat-shrinkable or heat-elasticizable. Furthermore, these elastic materials may be formed with gatherable layers, such as spunbonded polymer materials, as a neck-bonded laminate or a stretch-bonded laminate. For example, a suitable stretch-bonded laminate comprise two gatherable layers of 0.4 ounce per square yard (about 13.5 grams per square meter) of spunbond polypropylene having therebetween a layer of meltblown elastic material such as a Kraton elastic in either layer form or separate threads of material having a basis weight of about 0.5 ounce per square yard (about 16.9 grams per square meter). The layer of the elastomeric is stretched, the two layers of polypropylene then joined to the elastomeric layer, and upon relaxing the layers, the polypropylene layers gather. The materials may be breathable or nonbreathable.

The elastic members 30 of the present invention may be substantially entirely elastomeric, or alternatively, only certain areas of the elastic member 30 may be elastomeric. In particular, at least a part of the elastic members 30 may generally be elastic in the machine direction 28 or the cross-machine direction 29, or alternatively, at least a part of the elastic members 30 may be elastic in both the machine direction and the cross-machine direction 28 and 29. In a particular aspect, substantially the entire elastic member 30 may be elastomeric for improved performance.

In another aspect, different areas of the elastic member 30 may define differing levels of elasticity. For example, the outboard portions 32 of the elastic member may exhibit a greater level of elasticity than the inboard portion 34, or vice versa.

The elastic members 30 may initially be provided in the form of a continuously moving elastic material web 24, which may then be processed by the method and apparatus 40 of the present invention into individual elastic members 30. The elastic material web 24 may be provided by unwinding the elastic material web 24 and drawing the web 24 through the apparatus 40. Suitable unwinds (not shown) are well known to those skilled in the art, and can include a driven unwind, or a passive unwind that relies on the apparatus 40 to draw the web 24 through the process. Alternatively, the web 24 may pass through the apparatus 40 via a combination of a driven unwind and the draw of the apparatus 40.

Accordingly, the method and apparatus 40, as representatively illustrated in FIGS. 1 and 2, may further include a cutting assembly 75 to sever the continuously moving elastic material web 24 into the elastic members 30 that are eventually fed into the entry location 50 of the wheels 42 and 44. The cutting assembly 75 may be any mechanism known to those skilled in the art that can sever a web of material into discrete segments such as, for example, a rotary cutter.

For example, as representatively illustrated in FIG. 1, the cutting assembly 75 may include a die cutter 76 and a slip cutter 78 that are configured to first create the shape of the elastic members 30 in the elastic material web 24 and then sever the web 24 into discrete, spaced elastic members 30. For example, in a particular aspect, the die cutter 76 may form at least one line of weakness 74 in the elastic material 24. The line of weakness 74 can include a series of perforations, a continuous score line in the elastic material, an incomplete cut or break in the elastic material web 24, and the like, or combinations thereof. The at least one line of weakness 74 may define at least one of the leading edge 37 or the trailing edge 38 of the elastic member 30. The slip cutter 78 may then, in turn, cut through the elastic material web 24 in at least one location. The slip cutter 78 desirably has a tangential velocity that is higher than the tangential velocity of the die cutter 76, which desirably has a tangential velocity that is substantially similar or slightly faster than the elastic material web speed. As such, the slip cutter 78 may cut through the elastic material web 24 while accelerating the newly formed elastic member 30 thus separating the elastic member 30 from the elastic material web 24 at the line of weakness 74 and simultaneously spacing the discrete elastic members 30 from each other. Suitable die cutter and slip cutter assemblies are well known in the art. Alternatively, other cutting technology may be utilized such as water-cutting or laser-cutting.

The method and apparatus 40 of the present invention may further include an adhesive applicator assembly 70 that applies an operative amount of adhesive 72 to the elastic material web 24 or the elastic member 30 for attaching the elastic member 30 to the article web 20. For the sake of clarity, the adhesive will be particularly described as being applied to the elastic material web 24. Nonetheless, it will be readily understood by those of skill in the art that in the described embodiments, that an operative amount of adhesive 72 may be applied by the applicator assembly 70 to discrete elastic members 30 as well as on to the elastic material web 24 (prior to being separated into individual elastic members 30), or to the article web 20. This arrangement can depend, for example, on where the adhesive applicator 70 may be located relative to the cutting assembly 75 in the method and apparatus 40 of the present invention.

The adhesive applicator assembly 70 may include a bank of one or more adhesive heads for applying adhesive to the elastic members 30. The adhesive 72 may be applied to the elastic material web 24 in any number of selected patterns as are known to those skilled in the art. For example, as representatively illustrated in FIG. 1, the adhesive 72 may be applied in a generally rectilinear pattern. The adhesive applicator assembly 70 may apply the adhesive 72 in a spray pattern, a swirl pattern, slot coat, and the like or combinations thereof. In a particular aspect the adhesive may be applied using an EP-12 adhesive applicator assembly available from Nordson Corporation, a company having offices in Atlanta, Ga.

Moreover, the operative amount of adhesive 72 may advantageously be applied to the elastic material web 24 such that it is registered with the leading edge 37 and the trailing edge 38 of the elastic member 30. That is, the adhesive 72 may be applied intermittently only on those areas of the elastic material web 24 that will be processed by the apparatus 40 of the present invention into discrete elastic members 30 and are intended to be attached to an absorbent article, such as diaper 200. As such, during future processing in the method and apparatus 40 of the present invention, the adhesive 72 will be less likely to interfere with such processing. For example, as representatively illustrated in FIG. 1, the adhesive 72 may be applied to the elastic material web 24 prior to being separated into discrete elastic members 30. In such a configuration, the adhesive 72 may be applied to the web 24 in a registered manner such that the adhesive 72 would not interfere with or contact portions of the apparatus 40 that may be further downstream, such as the cutting apparatus 75, the wheels 42 and 44, or the transfer bands 60.

Alternatively, the elastic members 30 may be attached to the article web 20 by any suitable method known in the art, such as pressure bonding, ultrasonic bonding, welding, sewing, or mechanical bonding, and the like, or combinations thereof.

The various aspects of the present invention provide a method and apparatus for zone stretching an elastic member 30 and attaching it to a moving article web 20, such as a web of interconnected diapers. As used herein the term "zone stretch," "zone stretched," or "zone stretching" refers to the condition of an elastomeric component where at least one portion of the component has been elongated a greater amount than some other portion of the component, as well as the process for obtaining this condition in such a component. As such, in one aspect, at least one portion of the elastic member 30 is elongated, or stretched on the pair of wheels 42 and 44, while at least one other portion of the elastic member 30 remains substantially unstretched.

As discussed above, the elastic member 30 engages the wheels 42 and 44 at the entry location 50, and the width of the entry location (in the cross machine direction 29) is generally less than or equal to the width of the elastic member in the cross machine direction 29. As such, the inboard portion 34 is located in the space between the wheels 42 and 44 and the outboard portions 32 of the elastic member contact the outer surfaces of the wheels 42 and 44. As the wheels 42 and 44 rotate, the elastic member travels on the wheels 42 and 44 from the entry location 50 to the exit location 52. Simultaneously, since the space between the wheels in the cross machine direction is greater at the exit location 52 than at the entry location 50, the inboard portion 34 of the elastic member 30 is elongated or stretched by the pair of wheels 42 and 44, while the outboard portions remain substantially unstretched. The elastic member 30 is then attached to the article web 20 proximate to or downstream of the exit location 52.

For example, a nip may be created by placing an anvil roll 84 proximate the wheels 42 and 44 at the exit location 52 to allow the adhesive 72 to attach the elastic member 30 to the article web 20. In such a configuration, if the adhesive 72 is registered on the elastic member 30 to be placed proximate to the inboard portion of the elastic member, upon nipping, the inboard portion may gather and shirr a portion of the article web 20 while the outboard portions may remain free of attachment to the article web to provide a pair of elastomeric components. Alternatively, the elastic member 30 may be attached to the article web 20 in various other configurations. Similarly, the elastic member 30 may also be attached to the article web 20 by other attachment means such as ultrasonic bonding, welding, thermal bonding, sewing, and the like, or combinations thereof.

Thus, the inboard portion of the elastic member may be stretched while the outboard portions 32 remain substantially unstretched. In such a configuration, the elastic member 30 may be arranged to gather a portion of the article web 20 upon application while the unstretched portions may remain free from the article web to provide a pair of stretchable components on the article web. As will be described in greater detail below, an example of such an arrangement is a diaper 200 with a zone stretched elastic member 30 attached to the rear waist portion 204. In particular, the inboard portion of the elastic member 30 may be elongated or stretched by the method and apparatus 40 described herein, and may thus provide a gathered waist elastic 222 on the diaper 200, and the substantially unstretched outboard portions may extend beyond the diaper side portions 208 to provide a pair of elastomeric ears 226.

In another aspect, a portion of the elastic member 30, such as the inboard portion 34 may be stretched by the pair of rotating wheels 42 and 44 such that the elastic member 30 defines a stretched length in the cross machine direction 29 that is greater than the chassis width. The elastic member 30 may then be attached to the article web 20 by the method and apparatus 40 of the present invention. Thus, at least a portion of the elastic member 30, such as at least one of the outboard portions 32, may extend beyond the article web side edges 22. Moreover, in such an arrangement, the outboard portions 32 may also be further elongatable in use.

In one aspect the stretched portion of the elastic member 30 may be elongated at least 50%. In another aspect the stretched portion of the elastic member 30 may be elongated at least 100%. In still yet another aspect, the stretched portion of the elastic member 30 may be elongated at least 150%. In a particular aspect, the stretched portion of the elastic member may be elongated at least 200%.

As can be appreciated by one of skill in the art, the elastic member 30 may be zone stretched in various configurations. For example, the outboard portions 32 may be elongated while the inboard portion 34 remains substantially unstretched. In yet another alternative, both the inboard and outboard portions 34 and 32 may be elongated, with either the inboard or outboard portions 34 and 32 being elongated a greater amount.

In yet another aspect, the elastic member 30 may be further segmented into several areas having various degrees of elongation to arrive at a particular zone stretch arrangement. As such, a zone stretched elastic member 30 may be used to provide any number of suitable components on an article, such as a disposable absorbent article. Such an arrangement may be achieved, for instance, by having at least one additional wheel added to the pair of wheels 42 and 44. In such a configuration, each additional wheel would add additional portions to the elastic member 30.

Thus, the method and apparatus 40 may be utilized to apply an elastic member 30 to a continuously moving article web 20. For example, as representatively illustrated in FIG. 1, an elastic member 30 may be provided to the method and apparatus 40 of the present invention. As mentioned above, the elastic member 30 may be elongatable in at least a cross machine direction 29 and defines an elastic member 30 width. The elastic members 30 may be moved in an elastic member web path, as indicated by the arrow 26 via conveyors, vacuum conveyors, or as mentioned above, via a continuously moving elastic material web 24 that is provided to the apparatus 40.

In configurations where the elastic member 30 is provided by an elastic material web 24, a line of weakness 74 may be formed in the elastic material web 24 to define a trailing edge 38 in the elastic member 30. The elastic material web 24 may also be cut to define a leading edge 37 of the elastic member 30; the elastic material web 24 may then be separated at the line of weakness 74 into discrete elastic members 30.

The pair of rotatable wheels 42 and 44 may then be provided in the elastic member web path. The elastic member 30 may be engaged by the pair of wheels at the elastic member entry location 50. In one aspect, a portion of the elastic member 30 may be located beyond each of the inboard edges 46 of the pair of wheels 42 and 44 thereby defining a pair of outboard portions 32 of the elastic member 30 and an inboard portion 34 of the elastic member 30. The elastic member 30 may then be rotated by the pair of wheels 42 and 44 to the elastic member exit location 52. The elastic member 30 may then be applied to the article web 20 proximate to or downstream of the exit location 52. In another aspect, the outboard portions 32 may extend beyond the article web side edges 22.

Adhesive 72 may be applied to the elastic material web 24 or the elastic member 30 by providing the adhesive applicator assembly 70 in the process. In a particular aspect, an operative amount of adhesive 72 may be applied to the web 24 or to the elastic member 30 in an intermittent pattern such that the pattern of adhesive 72 is registered with the leading edge 37 and trailing edge 38 of the elastic member 30. Moreover, the intermittent pattern of adhesive 72 and the apparatus 40 may be configured so that the adhesive 72 does not contact parts of the apparatus 40 downstream of the adhesive applicator assembly 70, such as the wheels 42 and 44 or the cutting assembly 75.

As further indicated in FIG. 1, the elastic material web 24 may further pass through a cutting assembly 75 that may include a die cutter 76 and a slip cutter 78. The cutting assembly 75 may be configured to separate the elastic material web 24 into discrete elastic members 30.

The discrete elastic members 30 may then be transferred through the apparatus 40 by various suitable means. In one aspect, the elastic members 30 may be transferred via a vacuum transfer roll 82 or a transfer conveyor 80, or a combination thereof. Alternatively, the elastic members may be carried through the apparatus 40 by a vacuum transfer conveyor or direct transfer.

Thus, the elastic members 30 may be carried to the pair of rotating wheels 42 and 44. As representatively illustrated in FIG. 1, the elastic members may be engaged by the rotating wheels 42 and 44 at the entry location 50, and as the wheels 42 and 44 rotate, be zone stretched and applied to the continuously moving article web 20.

It will be readily apparent to those of skill in the art that the various steps of the method and the various components of the apparatus 40 need not be executed or placed in the order described above or as representatively shown in the illustrated embodiments. Instead, many alternate configurations are readily apparent. For example, the adhesive applicator assembly 70 may effectively be placed before or after the cutting assembly 75, or the wheels 42 and 44.

The zone stretched elastic member may be particularly suitable when used in connection with a disposable absorbent article. For instance, the article web may be a web of interconnected disposable absorbent articles, such as a disposable diaper 200 representatively illustrated in FIG. 3. As such, the article web 20 may be separated into a plurality of absorbent articles or diapers. The absorbent article 200 defines a front portion 202, a rear portion 204, and a crotch portion 206 connecting the front portion 202 and the rear portion 204. The absorbent article 200 includes a bodyside liner 210, an outer cover 212, and an absorbent core 214 located between the bodyside liner 210 and the outer cover 212. As used herein, reference to a front portion refers to that part of the absorbent article which is generally located on the front of a wearer when in use. Reference to the rear portion refers to the portion of the article generally located at the rear of the wearer when in use, and reference to the crotch portion refers to that portion which is generally located between the legs of the wearer when in use.

The crotch portion 206 has opposite longitudinal side portions 208 which may include a pair of elasticized, longitudinally extending leg elastics 218. The leg elastics 218 are generally adapted to fit about the legs of a wearer when in use and serve as a mechanical barrier to the lateral flow of body exudates. In addition, the leg elastics 218 may be provided by a zone stretched elastic member 30 as described herein.

The crotch portion 206 may also include a pair of longitudinally extending containment flaps 228. The containment flaps 228 are generally adapted to stand upright in at least the crotch portion and serve as a mechanical barrier to the lateral flow of body exudates. Such containment flaps 228 are well known in the art and are described in U.S. Pat. No. 4,704,116 issued Nov. 3, 1987, to Enloe, the disclosure of which is hereby incorporated by reference to the extent it is consistent (i.e. not in conflict) with the current disclosure.

The absorbent article 200 may further include a front waist elastic 220, back waist elastic 222 and pair of ears 226. The waist elastics 220 and 222 and the ears 226 may be provided by the zone stretched elastic member 30 of the present invention. For example, waist elastic structures are described in U.S. Pat. No. 4,916,005 to Lippert et al., the disclosure of which is hereby incorporated by reference to the extent it is consistent (i.e. not in conflict) with the current disclosure. Similarly, suitable ears 226 are described in U.S. Pat. No. 5,496,298 to Kuepper et al., the disclosure of which is hereby incorporated by reference to the extent it is consistent (i.e. not in conflict) with the current disclosure.

Alternatively, as representatively illustrated in FIG. 3, the back waist elastic 222 and pair of ears 226 may both be provided by a single zone stretched elastic member 30. For example, the inboard portion 34 may be elongated by the method and apparatus 40 of the present invention and provide a shirred, gathered back waist elastic 222. In addition, the outboard portions 32 may remain substantially unelongated by the method and apparatus 40 of the present invention. When the elastic member 30 is applied to the article web 20 by the method and apparatus 40, the outboard portions may extend beyond the side portions 208 of the diaper 200 to provide a pair of elastomeric ears 226.

A pair of fasteners 224 such as snap closures, hook and loop fasteners, mushroom fasteners or tape fasteners may be attached to the stretchable ears 226. The fasteners 224 are adapted to connect (desirably releasably connect) the front portion 202 to the rear portion 204 of the absorbent article 200, so as to fasten the article 200 about the waist of the wearer when in use.

The bodyside liner 210 of the absorbent article 200, as representatively illustrated in FIG. 3, suitably presents a body facing surface which is compliant, soft feeling, and non-irritating to the wearer's skin. Further, the bodyside liner 210 may be less hydrophilic than the absorbent core 214, to present a relatively dry surface to the wearer, and may be sufficiently porous to be liquid permeable, permitting liquid to readily penetrate through its thickness. A suitable bodyside liner 210 may be manufactured from a wide selection of web materials such as porous foams, reticulated foams, apertured plastic films, natural fibers (for example, wood or cotton fibers), synthetic fibers (for example, polyester or polypropylene fibers), or a combination of natural and synthetic fibers. The bodyside liner 210 is suitably employed to help isolate the wearer's skin from liquid held in the absorbent core.

Various woven and nonwoven fabrics can be used for the bodyside liner 210. For example, the bodyside liner may be composed of a meltblown or spunbonded web of polyolefin fibers. The bodyside liner 210 may also be a bonded carded web composed of natural and/or synthetic fibers. The bodyside liner 210 may be composed of a substantially hydrophobic material, and the hydrophobic material may, optionally, be treated with a surfactant or otherwise processed to impart a desired level of wettability and hydrophilicity. In a particular aspect of the present invention, the bodyside liner 210 comprises a nonwoven, spunbond, polypropylene fabric composed of about 2.8-3.2 denier fibers formed into a web having a basis weight of about 22 grams per square meter and a density of about 0.06 grams per cubic centimeter. The fabric may be surface treated with about 0.28 weight percent of a surfactant commercially available from Rohm and Haas Company under the trade designation Triton X-102.

The outer cover 212 of the absorbent article 200, as representatively illustrated in FIG. 4, may suitably be composed of a material which is either liquid permeable or liquid impermeable. It is generally preferred that the outer cover 212 be formed from a material which is substantially impermeable to liquids. For example, a typical outer cover can be manufactured from a thin plastic film or other flexible liquid impermeable material. For example, the outer cover 212 may be formed from a polyethylene film having a thickness of from about 0.012 millimeter (0.5 mil) to about 0.051 millimeter (2.0 mils). If it is desired to present the outer cover 212 with a more clothlike feeling, the outer cover 212 may comprise a polyethylene film having a nonwoven web laminated to the outer surface thereof, such as a spunbond web of polyolefin fibers. For example, a polyethylene film having a thickness of about 0.015 millimeter (0.6 mil) may have thermally laminated thereto a spunbond web of polyolefin fibers, which fibers have a thickness of about 1.5 to 2.5 denier per filament, which nonwoven web has a basis weight of about 24 grams per square meter (0.7 ounces per square yard). Methods of forming such clothlike outer covers are well known to those skilled in the art.

Further, the outer cover 212 may be formed of a woven or nonwoven fibrous web layer which has been totally or partially constructed or treated to impart a desired level of liquid impermeability to selected regions that are adjacent or proximate the absorbent core 214. Still further, the outer cover 212 may optionally be composed of a microporous "breathable" material which permits vapors to escape from the absorbent core 214 while still preventing liquid exudates from passing into the outer cover 212.

The absorbent core 214 of the absorbent article 200, as representatively illustrated in FIG. 4, may suitably comprise a fibrous web which includes a high absorbency material. As a general rule, the high absorbency material is present in the absorbent core 214 in an amount of from about 5 to about 100 weight percent based on total weight of the absorbent core to provide more effective performance. The absorbent core 214 may have any of a number of shapes. For example, the absorbent core 214 may be rectangular, I-shaped or T-shaped.

The outer cover 212 and bodyside liner 210 are generally adhered to one another so as to form a pocket in which the absorbent core 214 is located. Thus, the leg cuffs 216 are suitably formed by portions of the outer cover 212, and/or bodyside liner 210, which extend beyond the longitudinal sides of the absorbent core 214. Naturally, the leg cuffs 216 can also be formed from separate materials which are attached to the outer cover 212 and/or bodyside liner 210.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. A method for applying an elastic member to an article web defining a pair of article web side edges, said method comprising:
   i) providing said elastic member, said providing comprising:
      a) providing an elastic material web;
      b) forming a line of weakness in said elastic material web to define a trailing edge of the elastic member;
      c) cutting said elastic material web to define an leading edge of the elastic member; and
      d) separating said elastic material web at said line of weakness into discrete elastic members, wherein at least a portion of said elastic member is elongatable in at least a cross machine direction and defines an elastic member width;
   ii) moving said elastic member in a machine direction along an elastic member web path;
   iii) providing a pair of rotatable wheels in said elastic member web path, said pair of wheels defining:
      a) a pair of inboard edges,
      b) a pair of outboard edges opposite said inboard edges,
      c) an elastic member entry location having an elastic member entry location width that is less than said elastic member width, and
      d) an elastic member exit location having an elastic member exit location width that is greater than said elastic member entry width;
   iv) engaging said elastic member with said pair of wheels at said elastic member entry location wherein a portion of said elastic member is located beyond each of said inboard edges of said pair of wheels thereby defining a pair of outboard portions of said elastic member and an inboard portion of said elastic member;
   v) rotating said elastic member with said pair of wheels; and
   vi) applying said elastic member to said article web proximate said elastic member exit location wherein said outboard portions of said elastic member extend beyond said article web side edges.

2. The method of claim 1 further comprising:
   i) providing an adhesive application assembly; and
   ii) applying an operative amount of adhesive to said eiastic material web.

3. The method of claim 2 wherein said operative amount of adhesive is applied in a rectilinear pattern.

4. The method of claim 2 wherein said operative amount of adhesive is registered with said leading edge and said trailing edge.

5. The method of claim 2 wherein said operative amount of adhesive does not contact said pair of wheels.

6. The method of claim 1 wherein said trailing edge is curvilinear.

7. The method of claim 1 wherein said trailing edge defines w shape.

8. The method of claim 1 wherein engaging said elastic member comprises holding said elastic member on said pair of wheels with vacuum.

9. The method of claim 1 wherein engaging said elastic member comprises holding said elastic member on said pair of wheels with a pair of transfer bands.

10. The method of claim 9 wherein said pair of transfer bands wraps said pair of rotatable wheels at least between said entry location and said exit location.

11. The method of claim 9 comprising:
   i) providing an adhesive application assembly; and
   ii) applying an operative amount of adhesive to said web of elastic material; wherein said adhesive does not contact said pair of wheels or said transfer bands.

12. The method of claim 1 wherein rotating said elastic member with said pair of wheels elongates said inboard portion of said elastic member at least 50%.

13. The method of claim 1 wherein said pair of wheels each further define a wheel diameter of from between 0-3 meters to 2.0 meters.

* * * * *